US00PP35880P2

(12) United States Plant Patent
Ranney et al.

(10) Patent No.: US PP35,880 P2
(45) Date of Patent: Jun. 25, 2024

(54) ***X CHITALPA* PLANT NAMED 'NCXC1'**

(50) Latin Name: **x *Chitalpa tashkentensis***
Varietal Denomination: NCXC1

(71) Applicant: North Carolina State University, Raleigh, NC (US)

(72) Inventors: Thomas Green Ranney, Arden, NC (US); Richard Olsen, Arden, NC (US); Andra Windorf Nus, Arden, NC (US); Irene Palmer, Arden, NC (US); Nathan P. Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/206,260

(22) Filed: Jun. 6, 2023

(51) Int. Cl.
*A01H 5/02* (2018.01)
*A01H 6/00* (2018.01)

(52) U.S. Cl.
USPC ..... Plt./216

(58) Field of Classification Search
USPC ..... Plt./216, 226
CPC ..... A01H 5/02; A01H 5/00; A01H 6/00
See application file for complete search history.

(56) References Cited

PUBLICATIONS

Oregon State University Landscape Plants Chitalpa tashkentensis 'Pink Dawn' retrieved on Sep. 25, 2023 at https://landscapeplants.oregonstate.edu/plants/chitalpa-tashkentensis-pink-dawn, 3 pp. (Year: 2023).*

* cited by examiner

*Primary Examiner* — June Hwu
(74) *Attorney, Agent, or Firm* — Cassandra Bright

(57) ABSTRACT

A new and distinct cultivar of x *Chitalpa* plant named 'NCXC1' is disclosed, characterized by large inflorescences with vibrant purple flowers, and small tree habits. The new variety is an x *Chitalpa*, typically produced as an outdoor ornamental plant.

3 Drawing Sheets

Latin name of the genus and species: x *Chitalpa tashkentensis.*

Variety denomination: 'NCXC1'.

BACKGROUND OF THE INVENTION

The new cultivar is a product of a planned breeding program conducted by the inventors at a research nursery in Mills River, North Carolina. The objective of the breeding program was to produce new varieties with small tree habits and large, showy inflorescences. The crossing resulting in the new variety was made in 2005. The seed parent is the unpatented *Chilopsis linearis* 'Bubba'. The pollen parent is an unpatented, unnamed selection of the variety *Catalpa* x *galleana*. Per common taxonomical reference, the new variety is an x *Chitalpa tashkentensis.*

The new variety was found and selected by the inventors in 2006 at the same nursery in Mills River, North Carolina.

Asexual reproduction of the new cultivar 'NCXC1' was first performed during June of 2010 in Mills River, North Carolina, by softwood cuttings treated with a basal dip of 5,000-7,000 ppm indole butyric acid (potassium salt) in water. Through subsequent propagation, multiple additional generations have been reproduced, having shown that the unique features of this cultivar are stable and reproduced true to type.

Date of first sale was Jun. 21, 2022, in Grand Haven, Michigan. This sale was made directly by the inventor or one who obtained the claimed invention directly or indirectly from the inventor. This sale and all public disclosures made between Jun. 21, 2022 and the filing of this application fall within the exception allowed under 102(b)(1).

SUMMARY OF THE INVENTION

The cultivar 'NCXC1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCXC1.' These characteristics in combination distinguish 'NCXC1' as a new and distinct x *Chitalpa* cultivar:

1. Small tree habit.
2. Large inflorescences.
3. Vibrant purple flowers.

PARENT COMPARISONS

Plants of the new cultivar x *Chitalpa* 'NCXC1' can be compared to the seed parent in most horticultural characteristics, however, plants of 'NCXC1' differ in the following:

1. Mature tree height of the new variety(6 meters) is generally shorter than the height of the seed parent(3 to 8 meters).
2. Inflorescences of the new variety produce more flowers (about 60) than inflorescences of the seed parent(12 to 15).

3. Foliage shape of the new variety is ovate, while the foliage shape of the seed parent is linear.

Plants of the new cultivar x *Chitalpa* 'NCXC1' can be compared to the pollen parent in most horticultural characteristics, however, plants of 'NCXC1' differ in the following:

1. Mature tree height of the new variety(6 meters) is generally shorter than the height of the pollen parent (3.5 to 16 meters).
2. Inflorescences of the new variety produce fewer flowers(about 60) than the inflorescences of the pollen parent(50 to 180).
3. Corolla lobe color of the new variety is purplish-red, while the corolla lobe color of the pollen parent is white.

COMMERCIAL COMPARISON

Plants of the new cultivar x *Chitalpa* 'NCXC1' can be compared to the commercial variety x *Chitalpa* 'Pink Dawn', unpatented. Plants of 'NCXC1' are similar to plants of 'Pink Dawn' in most horticultural characteristics, however, plants of 'NCXC1' differ in the following:

1. Corolla lobe color of the new variety is purplish-red, while the corolla lobe color of this comparator is light pink to light lavender.
2. Inflorescences of the new variety produce more flowers (about 60) than inflorescences of this comparator(15 to 40).
3. Foliage shape of the new variety is ovate, while the foliage shape of this comparator is lanceolate.

BRIEF DESCRIPTION OF THE PHOTOGRAPHS

The photographs were taken using conventional techniques and although colors may appear different from actual colors due to light reflectance it is as accurate as possible by conventional photographic techniques.

DETAILED BOTANICAL DESCRIPTION

Figure 1:
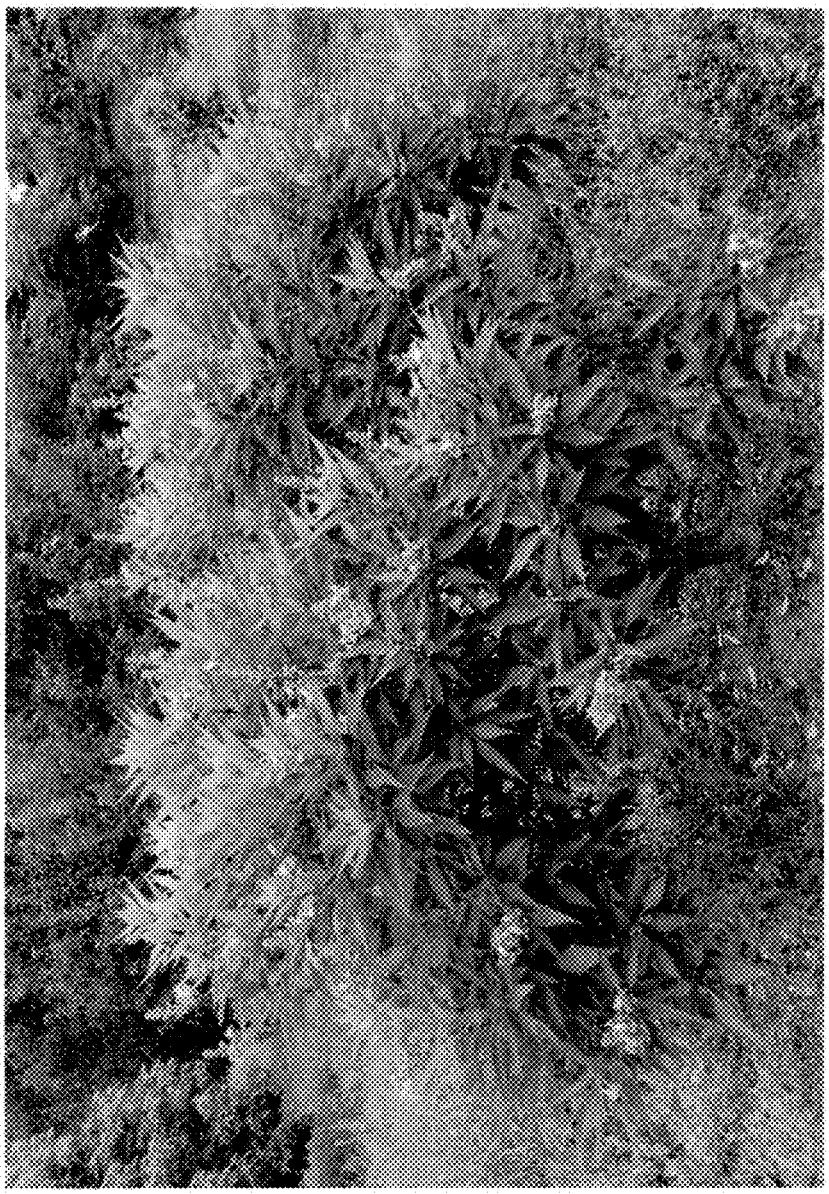
FIG. 1 is a color photograph showing a five-year-old field-grown tree in spring of 2022, in Mills River, North Carolina.
Figure 2:
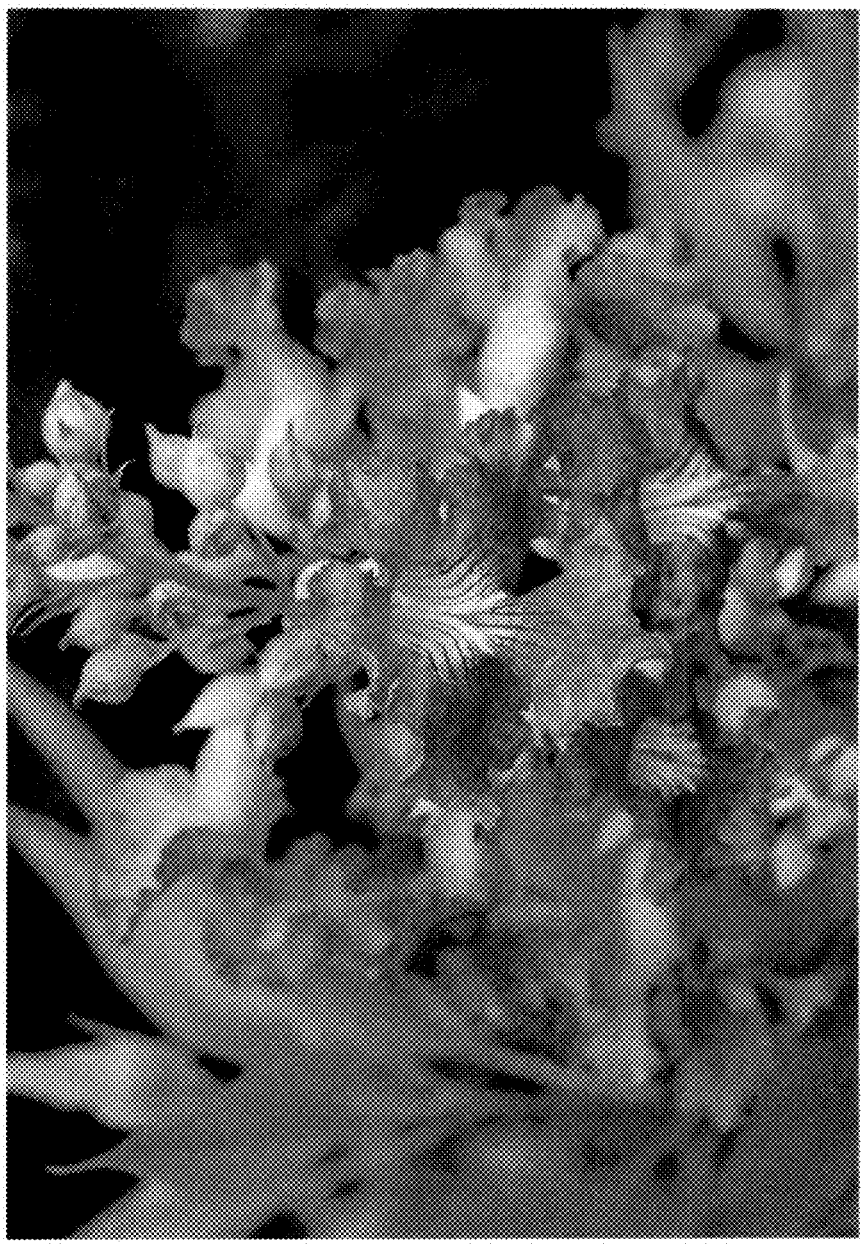
FIG. 2 is a photograph of a flower of a five-year-old field-grown tree in the spring of 2022, in Mills River, North Carolina.
Figure 3:
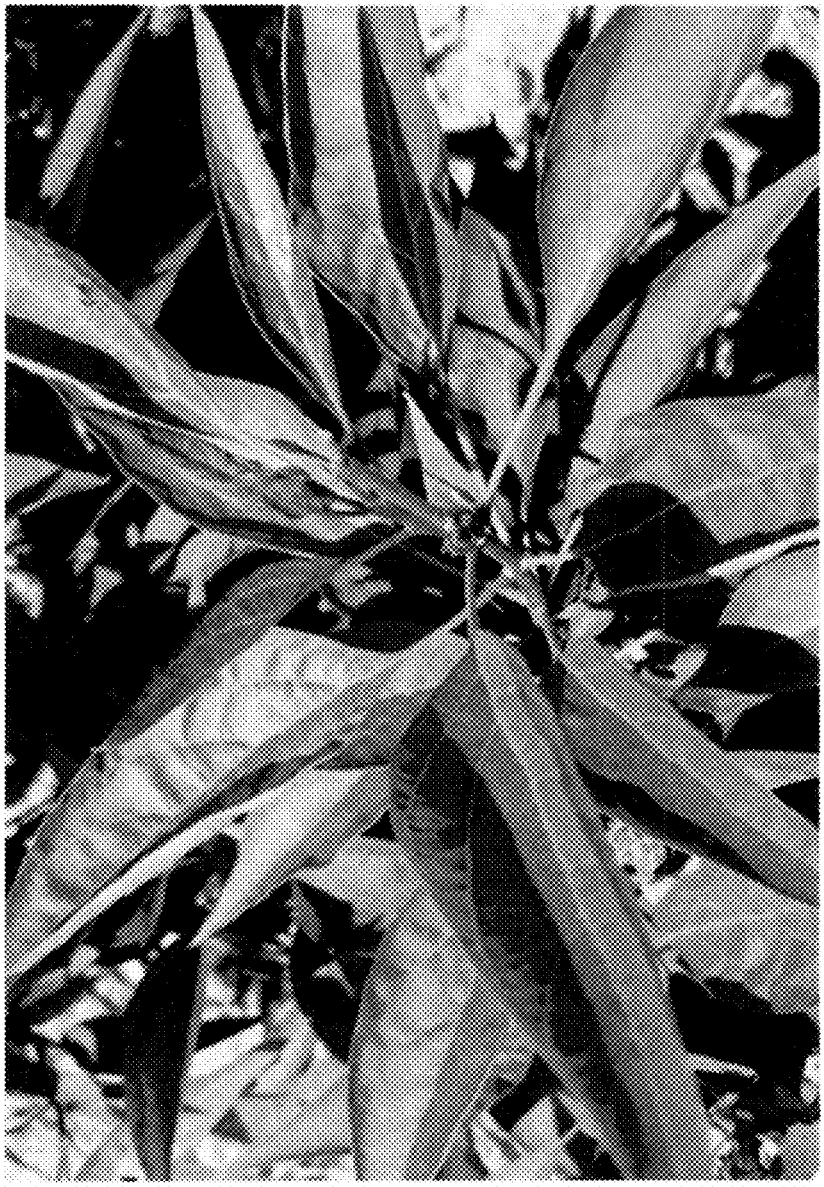
FIG. 3 is a color photograph of the clean foliage of a five-year-old field-grown tree in spring of 2022, in Mills River, North Carolina.

In the following description, color references are made to The Royal Horticultural Society Colour Chart 2015, except where general terms of ordinary dictionary significance are used. The following observations and measurements describe 'NCXC1' plants grown outdoors in Mills River, North Carolina. The plants were about 5 years old. Temperatures ranged from 5° C. to 10° C. at night to 18° C. to 27° C. during the day. No artificial light, photoperiodic treatments were given to the plants. Measurements and numerical values represent averages of typical plant types. Botanical classification: x *Chitalpa tashkentensis* 'NCXC1'.

PROPAGATION

Typical method: Softwood cuttings.

PLANT

Growth habit: Small ornamental flowering tree.

Height: About 2 meters after 5 years. Estimated mature height of about 6 meters.

Plant spread: About 1.5 meters after 5 years.

Age of plant described: Approximately 5 years.

Shoots:

Current year's growth:

*Length.*—Average 18 cm.

*Diameter.*—Average 0.2 cm.

*Color.*—RHS Yellow-Green 146C.

*Texture.*—Sparsely hirsute.

Prior year's growth:

*Length.*—Average 9.5 cm.

*Diameter.*—About 0.5 cm.

*Color.*—RHS Grey-Brown 166A.

*Texture.*—Sparsely hirsute.

Branches:

*Woody branches* 2-4 years old:

*Length.*—Average 27 cm.

*Diameter.*—Average 1.1 cm.

*Color.*—RHS Brown N199A.

*Texture.*—Glabrous with narrowly elliptic (0.15 cm×0.1 cm) lenticels of RHS Brown 199C.

Trunk (measured 0.5 meter from ground on a 5-year-old tree):

*Diameter.*—About 4 cm.

*Color.*—RHS Brown N199A.

*Texture.*—Rough-textured with vertical furrows of RHS Brown 199A.

Internode length: Average 1.7 cm.

FOLIAGE

Leaf:

*Type.*—Simple.

*Arrangement.*—Opposite, sometimes whorled.

*Persistence.*—Deciduous.

*Shape.*—Ovate.

*Length.*—Average 14.6 cm.

*Width.*—Average 4.6 cm.

*Apex.*—Acuminate.

*Base.*—Cuneate.

*Margin.*—Entire.

*Texture.*—Glabrous, both sides.

*Color.*—Upper Side: RHS Green 137B. Under Side: RHS Yellow-Green 146A.

*Fall color.*—Leaves turn brown and shrivel, no significant Fall foliage color.

*Venation.*—Type: Pinnate. Color: Upper side: RHS Green 137B. Under side: RHS Yellow-Green 146C.

Petiole:

*Length.*—Average 3.7 cm.

*Diameter.*—About 0.15 cm.

*Color.*—RHS Yellow-Green 146C.

*Texture.*—Finely pubescent.

Dormant leaf bud:
*Length.*—About 1 mm.
*Diameter.*—About 2 mm.
*Color.*—Near RHS Brown N200A.
*Texture.*—Sparsely pubescent.

INFLORESCENCE

Natural flowering season: June in Mills River, North Carolina.
Inflorescence type: Flowers arranged in a thyrse, a compact panicle with indeterminate main axis and determinate sub axes.
Quantity of flowers per inflorescence: About 60.
Inflorescence length: Average 23 cm.
Inflorescence diameter: Average 12 cm.
Fragrance: None.
Lastingness of individual flowers: About 7 days.
Bud:
*Length.*—About 1 cm.
*Diameter.*—About 1.5 cm.
*Shape.*—Onion-shaped.
*Color.*—RHS Red 183D.
*Texture.*—Glabrous.
Flower:
*Arrangement.*—Funnel-form with two smaller upper lobes and three larger lower lobes.
*Length.*—Average 4.5 cm.
*Width.*—Average 5 cm.
*Two upper lobes.*—Shape: Ovate. Margin: Undulate. Length: Average 1.8 cm. Width: Average 1.8 cm. Texture: Glabrous. Color: RHS Purple-Red 70A, both upper and lower surfaces.
*Three lower lobes.*—Shape: Ovate. Margin: Undulate. Length: Average 2.1 cm. Width: Average 2.2 cm. Texture: Glabrous. Color: RHS Purple-Red 70A, both upper and lower surfaces.
*Throat color.*—RHS White N155B, specked and striped with Red-Purple N77A, and two Yellow 7B stripes.
*Corolla tube.*—Length: About 2 cm. Width: About 1 cm. Color: Near RHS N155B. Texture: Glabrous.
Calyx/sepals:
*Quantity of sepals.*—2, forming a 2-lobed calyx.
*Length.*—About 1 mm.
*Width.*—About 2 cm.
*Color.*—Near RHS Yellow-Green 146C.
*Texture.*—Pubescent.
Peduncle:
*Length.*—Average 1.8 cm.
*Diameter.*—About 0.15 cm.
*Texture.*—Pubescent.
*Color.*—RHS Yellow-Green 146C.
Pedicel:
*Length.*—Average 0.7 cm.
*Diameter.*—About 0.1 cm.
*Texture.*—Pubescent.
*Color.*—RHS Yellow-Green 146C.

REPRODUCTIVE ORGANS

Gynoecium:
*Pistil number.*—1.
*Pistil length.*—About 2.5 cm.
*Stigma color.*—RHS Greenish White 165C.
*Style length.*—About 2.0 cm.
*Style color.*—RHS Greenish White 165C.
Androecium:
*Stamen number.*—2 fertile stamens and 1 or 2 staminodes.
*Anther size.*—About 0.4 cm.
*Anther color.*—RHS Greenish White 165C.
*Pollen color.*—RHS Light Yellow 162C.

OTHER CHARACTERISTICS

Disease resistance: Neither resistance nor susceptibility to the normal diseases and pests of *Chitalpa* has been observed.
Drought tolerance and cold tolerance: At least USDA zone 6b; testing has not been completed in colder zones.
Fruit/seed production: Not observed.

What is claimed is:

1. A new and distinct cultivar of x *Chitalpa* plant named 'NCXC1' as herein illustrated and described.

* * * * *